US008260005B2

(12) United States Patent
Tomic et al.

(10) Patent No.: US 8,260,005 B2
(45) Date of Patent: Sep. 4, 2012

(54) PORTABLE TOOL FOR DETERMINING MEAT QUALITY

(75) Inventors: Gerda Roxana Tomic, Santiago (CL); Renato Salinas, Santiago (CL); José Rolando Silva, Santiago (CL); Fernando Osorio, Santiago (CL); Héctor Barrera, Santiago (CL)

(73) Assignee: Universidad De Santiago De Chile, Santiago (CL)

( * ) Notice: Subject to any disclaimer, the term of this patent is extended or adjusted under 35 U.S.C. 154(b) by 1162 days.

(21) Appl. No.: 12/059,369

(22) Filed: Mar. 31, 2008

(65) Prior Publication Data

US 2008/0247603 A1  Oct. 9, 2008

Related U.S. Application Data

(60) Provisional application No. 60/909,222, filed on Mar. 30, 2007.

(51) Int. Cl.
*G06K 9/00* (2006.01)

(52) U.S. Cl. ........ 382/110; 382/155; 382/156; 382/157; 382/159

(58) Field of Classification Search .......... 382/110, 382/155–160
See application file for complete search history.

(56) References Cited

U.S. PATENT DOCUMENTS

| 5,303,708 | A | * | 4/1994 | Stouffer | 600/437 |
| 5,944,598 | A | * | 8/1999 | Tong et al. | 382/100 |
| 6,104,827 | A | * | 8/2000 | Benn et al. | 382/110 |
| 6,198,834 | B1 | * | 3/2001 | Belk et al. | 382/110 |
| 6,732,119 | B2 | * | 5/2004 | Ganapathy et al. | 382/162 |
| 6,751,364 | B2 | | 6/2004 | Haagensen et al. | |
| 6,891,961 | B2 | * | 5/2005 | Eger et al. | 382/110 |
| 2004/0091587 | A1 | * | 5/2004 | Sewalt et al. | 426/240 |

OTHER PUBLICATIONS

Jinglu Tan, "Meat Quality Evaluation by Computer Vision", Journal of Food Engineering, vol. 61 Issue 1, Jan. 2004, pp. 27-35.*
Kazuhiko Shiranita, Kenichiro Hayashi, Akifumi Otsubo, Tsuneharu Miyajima and Ryuzo Takiyama, "Grading Meat Quality by Image Processing", The Journal of the Pattern Recognition Society, vol. 33 Issue 1, Jan. 2000, pp. 97-104.*
M.J. Van Oeckel, N. Warnants and Ch.V. Boucqué, "Measurement and Prediction of Pork Colour", Meat Science vol. 52, Issue 4, Aug. 1999, pp. 347-354.*
Cernadas et al., Recognizing marbling in dry-cured Iberian ham by multiscale analysis, Pattern Recognition Letters, Elsevier, 2002, vol. 23, pp. 1311-1321.
Jeyamkondan et al., Predicting Beef Tenderness with Computer Vision, The Society for Engineering in Agricultural, Food, and Biological Systems, 2001 ASAE Annual International Meeting, Sacramento, California, Jul. 30-Aug. 1, 2001, Paper No. 01-3063, 10 pages.

(Continued)

*Primary Examiner* — Matthew Bella
*Assistant Examiner* — Eric Rush
(74) *Attorney, Agent, or Firm* — Hasse & Nesbitt LLC; Daniel F. Nesbitt (57) ABSTRACT

A system, method and device for grading of meat such as bovine, porcine, sheep, horse or poultry meat among others. The device of this invention is a portable tool, which is approached toward a meat specimen to be analyzed and captures an image. The device then objectively relates the image to meat quality parameters by means of an image analyzing method. The device and method solve, in a practical, fast and satisfactory way, the problem of determining meat quality parameters such as texture, color, and contained intramuscular fat percentage.

4 Claims, 6 Drawing Sheets

OTHER PUBLICATIONS

Tang et al., Classification of Broadleaf and Grass Weeds using Gabor Wavelets and an Artificial Neural Network, American Society of Agricultural Engineers, 2003, vol. 46(4), pp. 1247-1254.

Yoshikawa et al., Feature Extraction Algorithm for Beef Marbling, 1999 IEEE Pacific Rim Conference on Communications, Computers and Signal Processing, Aug. 22-24, 1999, Victoria, British Columbia, pp. 209-212. (cover + 4 pages).

Arul et al., Characterization of Beef Muscle Tissue Using Texture Analysis of Ultrasonic Images, 1993 Proceedings of the Twelfth Southern Biomedical Engineering Conference, Apr. 2-4, 1993, pp. 141-143. (1 page).

Belk et al., Evaluation of the Tendertec beef grading instrument to predict the tenderness of steaks from beef carcasses, Journal of Animal Science, 2001, vol. 79, Issue 3, pp. 688-697. (1 page).

Buche et al., Quantitative characterization of muscle fiber by image analysis, Computers and Electronics in Agriculture, Feb. 1997, vol. 16, Issue 3, pp. 189-217. (1 page).

Cannell et al., Online evaluation of a commercial video image analysis system (Computer Vision System) to predict beef carcass red meat yield and for augmenting the assignment of USDA yield grades. United States Department of Agriculture. Journal of Animal Science, 2002, vol. 80, Issue 5, pp. 1195-1201. (1 page).

Chandraratne et al., Determination of Lamb Grades Using Texture Analysis and Neural Networks, Proceedings of the $3^{rd}$ IASTED International Conference, Visualization, Imaging and Image Processing, Sep. 8-10, 2003, Benalmadena, Spain, pp. 656-661.

Cross et al., Objective measurements of carcass and meat quality, Meat Science, 1994, vol. 36, Issues 1-2, pp. 191-202. (1 page).

Li et al., Classification of tough and tender beef by image texture analysis, Meat Science, Apr. 2001, vol. 57, Issue 4, pp. 341-346. (1 page).

Porter et al., A Robust Automatic Clustering Scheme for Image Segmentation Using Wavelets, IEEE Transactions on Image Processing, Apr. 1996, vol. 5, No. 4, pp. 662-665.

Shackelford et al., Coupling of image analysis and tenderness classification to simultaneously evaluate carcass cutability, longissimus area, subprimal cut weights, and tenderness of beef, Journal of Animal Science, 1998, vol. 76, Issue 10, pp. 2631-2640. (1 page).

Shiranita et al., Determination of Meat Quality by Image Processing and Neural Network Techniques, *FUZZ IEEE 2000. The Ninth IEEE International Conference* on Fuzzy Systems, May 7-10, 2000, San Antonio, Texas, vol. 2, pp. 989-992. (1 page).

Tomic et al., Rapid Analysis and Information Fusion for Quantification of Intramuscular Fat Content, Proceedings of the Sixth International Conference of Information Fusion, 2003, vol. 1, pp. 358-363. (1 page).

Unser, Michael, Texture Classification and Segmentation Using Wavelet Frames, IEEE Transactions on Image Processing, Nov. 1995, vol. 4, No. 11, pp. 1549-1560.

Wulf et al., Using objective measures of muscle color to predict beef longissimus tenderness, Journal of Animal Science, 1997, vol. 75, Issue 3, pp. 684-692. (1 page).

\* cited by examiner

PORTABLE TOOL FOR DETERMINING MEAT QUALITY

CROSS-REFERENCE TO RELATED APPLICATION

This application claims the benefit of U.S. Provisional Application No. 60/909,222, filed Mar. 30, 2007.

BACKGROUND OF THE INVENTION

U.S. Pat. No. 6,751,364 (incorporated herein by reference) divulges an image analysis system and method for the grading of meat, predicting quality of meat and/or predicting meat yield of an animal. One embodiment of the invention is particularly designed to capture an image of the $12^{th}$ rib cross section of the ribeye and perform an image analysis of the ribeye for grading purposes. The image capturing camera portion of the system has a wedged shaped camera housing for easy of insertion into the ribbed incision. Once the image is captured either digitally or captured and converted to a digital image, an image analysis is performed on the digital image to determine parameters such as the percent lean, total area of the ribeye, total fat area, total lean area, percent marbling, and thickness of fat adjacent to the ribeye, and other parameters. These parameters are used to predict value determining traits of the carcass.

BRIEF DESCRIPTION OF THE INVENTION

The present invention relates to a portable device for determining meat quality with possible minimum error, thus replacing a human grader with computer-assisted grader (artificial vision). Analyzed meat may be bovine, porcine, sheep, horse or poultry meat.

The present application implies developing a new method of measuring parameters such as meat fat, texture and color by means of a method that allows relating said meat quality parameters to values obtained from images.

DETAILED DESCRIPTION OF INVENTION

The present description comprises some specific technical terms, which will be detailed below in order to avoid misinterpretations regarding other uses thereof or meanings that can be connected to the same terms.

The term "artificial vision" refers to the image captured by an electronic device and the computational interpretation of said image. This term is also known as "computer vision", and corresponds to a sub-field of artificial intelligence. The purpose of the artificial vision is programming a computer, which due to said programming should "understand" a scene or image features.

The term "channel" refers to a primary meat unit from an animal that was insensitized, bled, skinned, and gutted, where its head was cut at the atlanto-occipital joint, its external genital organs were also cut as well as its limbs, which were cut at carpometacarpal and tarso-metatarsal joints.

The term "meat texture" refers to the sensorial manifestation of foodstuff structure and the way it reacts before the application of forces, such as shear stress. It is considered a food-grade parameter, since it directly produces an effect on the palatability, and said effect is noted only when meat has been subjected to a boiling process. It is directly determined by properties of conjunctive myofibril structures of the cytoskeleton, which differ greatly and depend on specie, race, gender, and age, thus producing an effect on technological and biological variables.

The term "intramuscular fat percentage", also referred as marbling, relates to the visible fat amount in a meat cut. Intramuscular fat amount produces an effect on meat flavor, tenderness and juicy character, mainly depending on gender, slaughtering age and principally on genetic type. Meat fat quality basically depends on feedstuff composition consumed by the animal during the fattening stage.

Terms such as "color space", "color modules" or "color systems" correspond to a coordinate system and an area or sub-space within said system, where each color is represented by a single point. A color space allows specifying and visualizing any color. Psycho-physical parameters of color perception are three: brightness, tone, and saturation. In the present invention use of color spaces are as follows:

Color space RGB, which is based on the combination of three different chromatic luminance signals: red (R), green (G), and blue (B). Graphically it is represented by a cube. Gray tones are represented by a straight line linking origin (0, 0, 0) with point (255, 255, 255) over which the three color components have the same magnitude. This corresponds to coordinated space used by electronic devices such as digital cameras and monitors.

Color space "XYZ" utilizes a brightness component (component "Y") and two coloring or chromaticity components, which corresponds to components "X" and "Z". Components "X", "Y", and "Z" have a value ranging from 0 to 100. Values of each component are obtained by means of integration or adding, which involves a lighting source, object reflectance, and sensitivity curves of a standard human observer. Quantitative colorimetry utilizes three data pieces to calculate colors: the energy of the luminous source (400 to 700 nm), the reflectance of the object and the curves of sensitivity of the eye.

Color space "Lab" represents colors by means of the scale of Hunter Lab, which is one of the easiest scales to interpret in the food industry. It uses parameters L, a, and b, where "L" measures the luminosity in a scale from 0 to 100, where 100 represents the color white and 0 represents the color black, "a" measures red tonalities (+127) until green (-128), and "b" measures yellow tonalities (+127) until blue (-128).

Lab coordinates can be obtained by means of mathematical formulae from values of coordinates XYZ and values of $X_0$, $Y_0$, $Z_0$, that represent the "white pattern" of the system, for example:

$$L^* = 116 - (Y/Y_0)^{1/3} - 16$$

$$a^* = 500 \cdot [(X/X_0)^{1/3} - (Y/Y_0)^{1/3}]$$

$$b^* = 200 \cdot [(Y/Y_0)^{1/3} - (Z/Z_0)^{1/3}]$$

The term "image segmentation" refers to the technique by which an object of interest in an image can be separated from the "background" of the image. It does not necessarily identify the object category. For example, if it relates to a character like the letter "A", the segmentation only identifies the image area where it is possible to find this character.

From the image a pair of referential points or pixels is selected (the corresponding minimum and maximum value in gray scale).

Each point or pixel of the image is selected according to its proximity with respect to these referential points.

Accordingly, the image points are separated in two categories, which show a similarity in their values of gray level. Particularly, these categories correspond to the group of pixels that correspond to meat and the pixels that do not correspond to meat, i.e., they correspond to the image background.

The term "thresholding" refers to a technique used in image segmentation. Thresholding is the method by which a level of threshold "T" is chosen in order to classify each pixel of the image $f(x,y)$. If the pixel meets or exceeds the threshold property, for example $f(x,y)>T$, then the pixel is assigned to the object class; otherwise, the pixel is assigned to the background class.

For example, the Otsu's method may be used as a thresholding method. This is an iterative method that calculates an optimal threshold for a standardized histogram comprising two pixel distributions. The method assumes that the histogram is formed by two Gaussian curves, and that threshold T shall minimize the weighted sum of each one of the variances of the present objects.

Device Definition

The objective of the present invention relates to producing a portable device for determining meat quality with the minimum possible error, thus replacing a human grader with a computer-assisted grader (artificial vision). This invention also relates to a method of measuring parameters such as meat fat, texture and color by relating meat quality parameters to values obtained from images captured by a portable device.

The present invention consists of a system capable of objectively measuring meat quality parameters, and use of an image analyzing method captures images of meat quality parameters with no need to manipulate the meat.

The system of the present invention comprises a portable device which captures images of a meat specimen to be analyzed; and uses an image analyzing method to determine meat quality parameters that are measured using understandable units of the meat industry. Finally, the obtained results are displayed on a screen.

Figure 1:
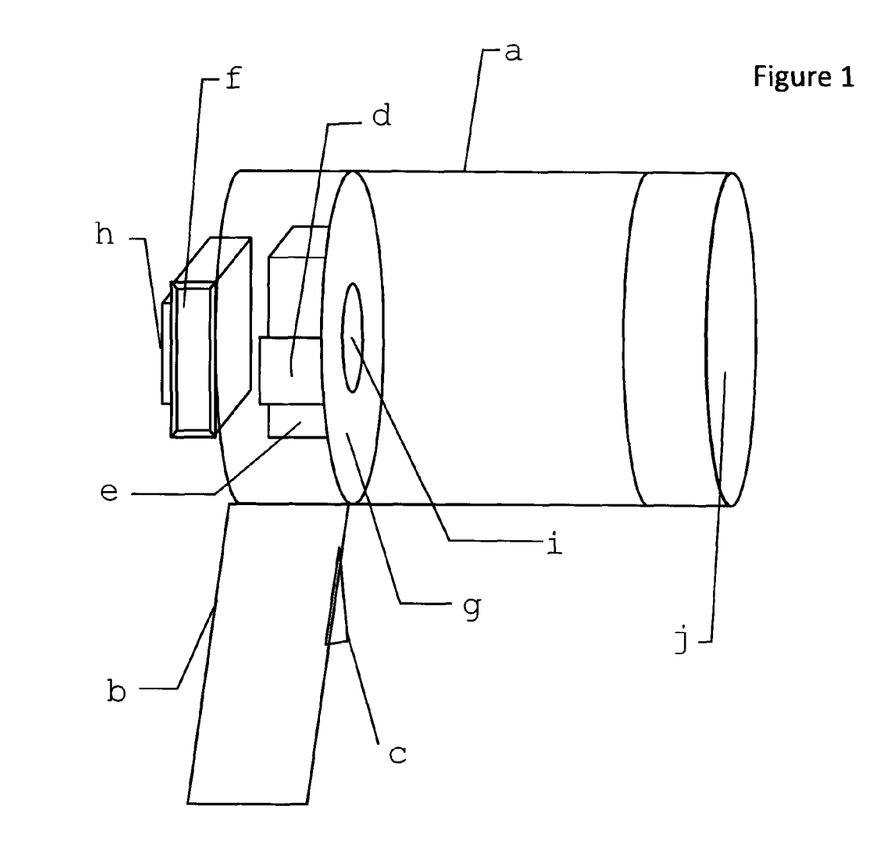
FIG. 1 is the device of the present invention.
Figure 2:
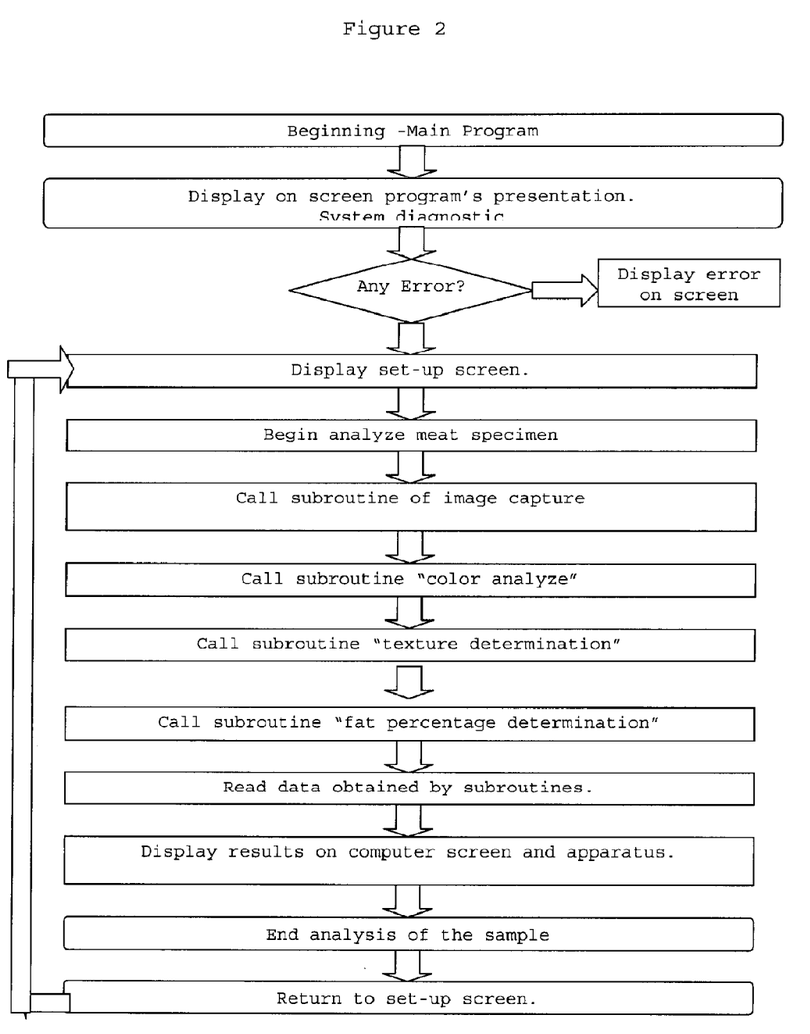
FIG. 2 is the main flow diagram of color, texture, and intramuscular analysis of a meat specimen.
Figure 3:
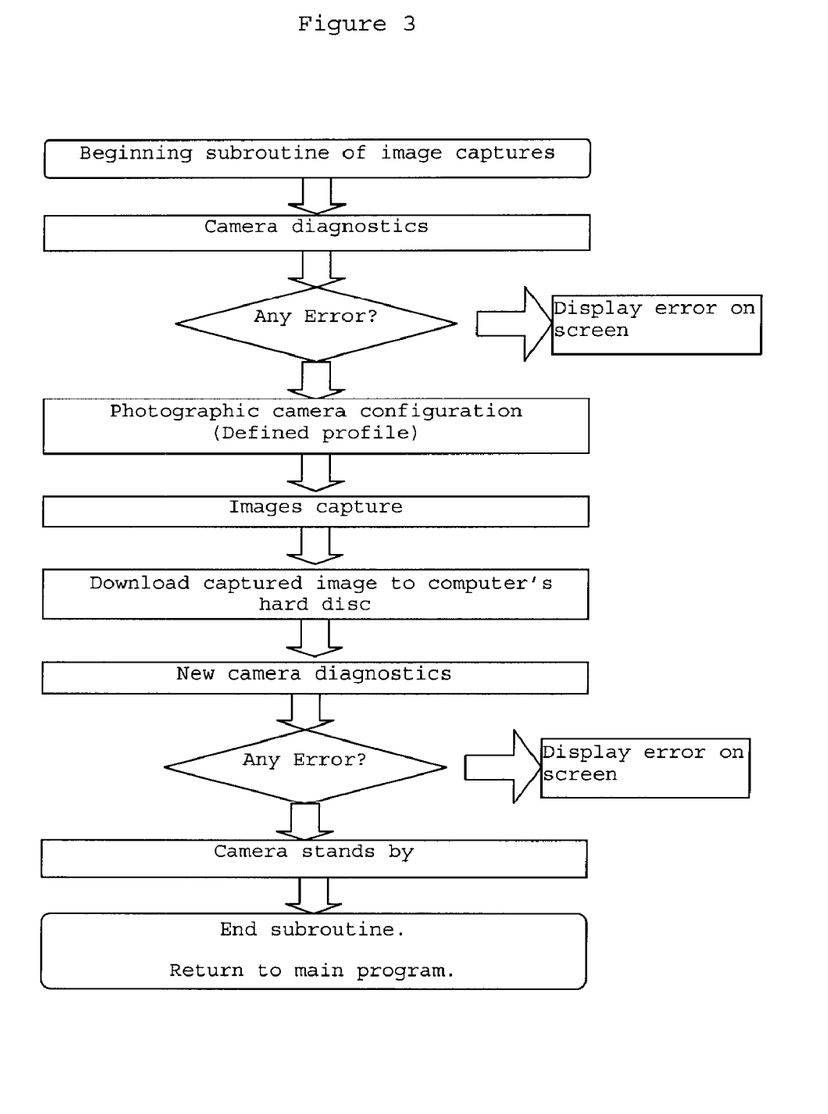
FIG. 3 is a flow diagram of sub-routine capture of digital image.
Figure 4:
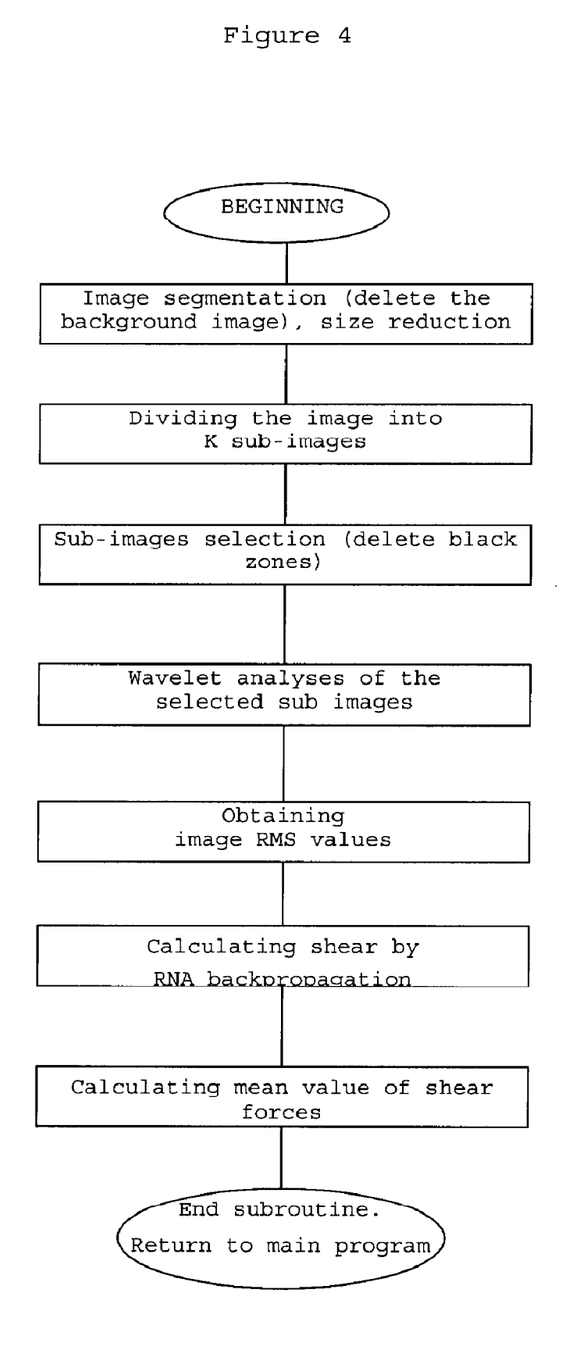
FIG. 4 is a flow diagram of sub-routine that determines texture values.
Figure 5:
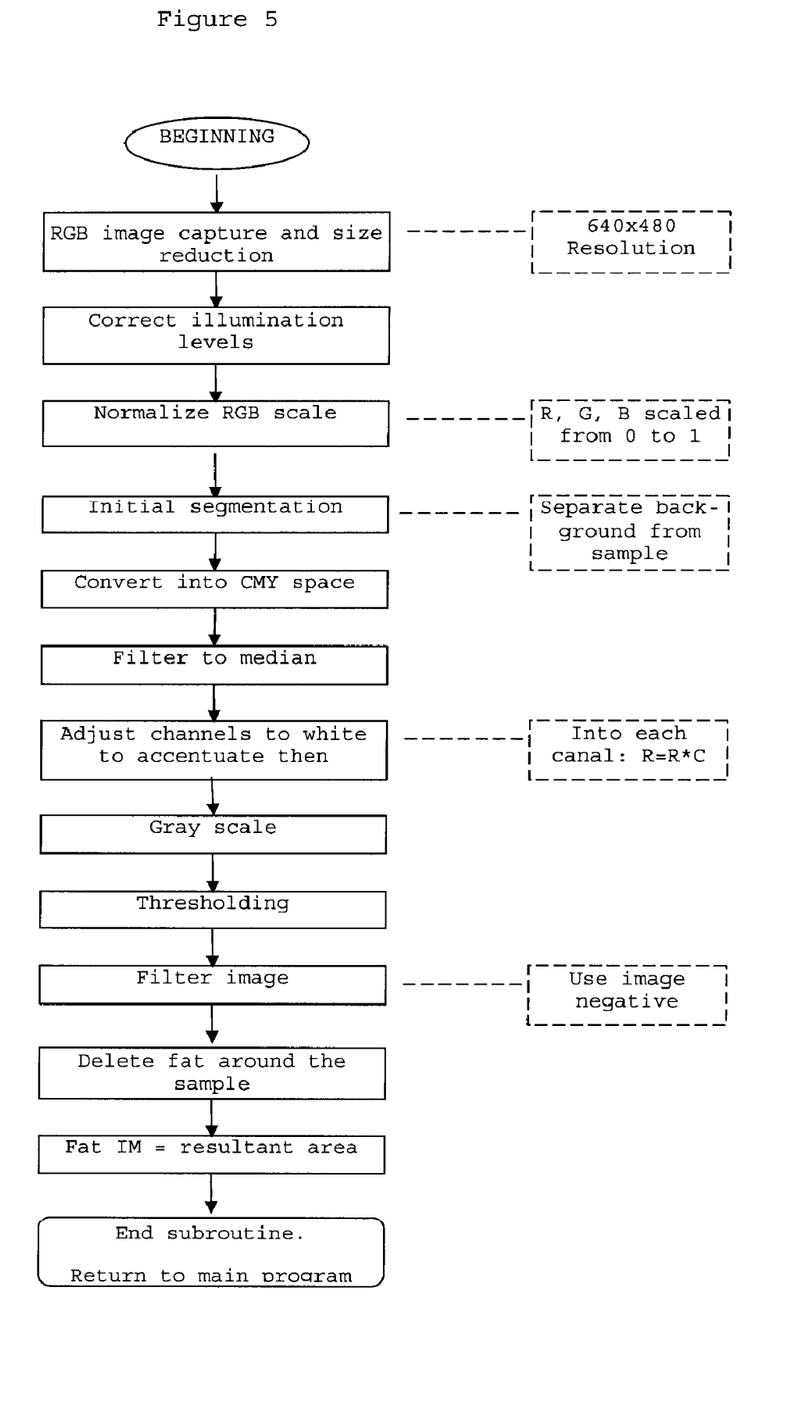
FIG. 5 is a flow diagram of sub-routine that determines intramuscular fat percentage.
Figure 6:
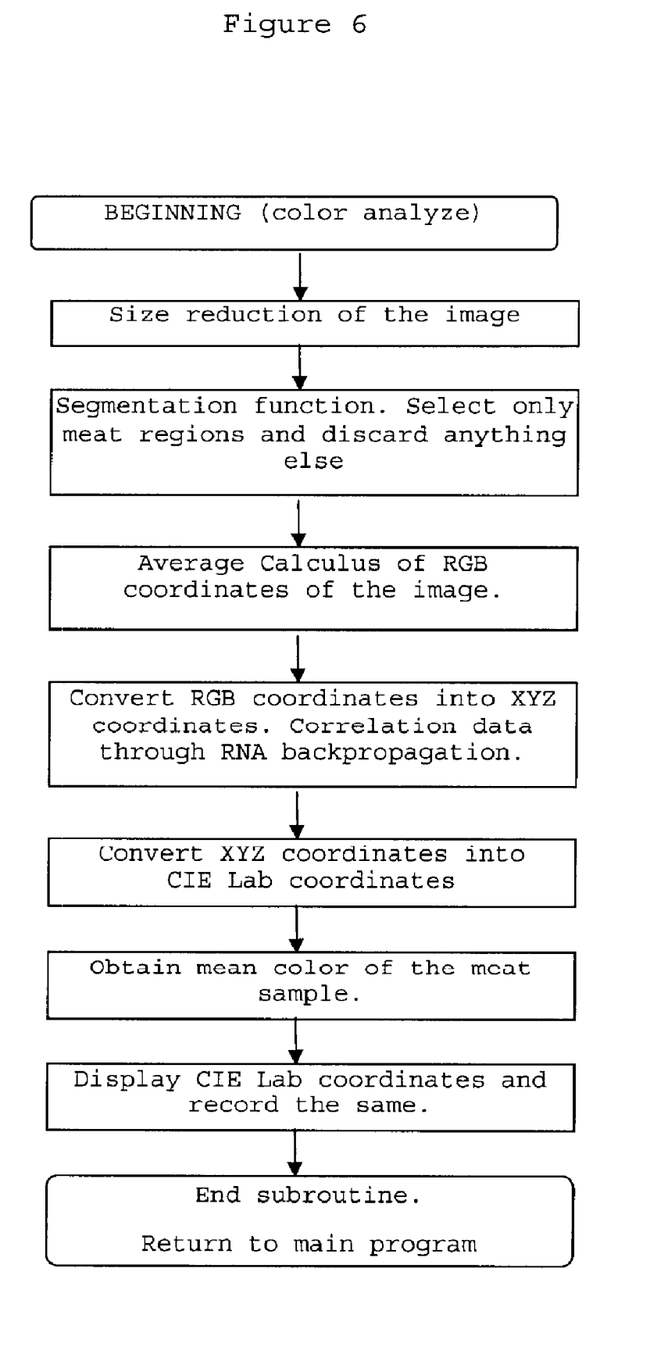
FIG. 6 is a flow diagram of sub-routine that determines color (CIE-Lab coordinates).

The present portable device (FIG. 1) consists of a casing, preferably a tubular-shaped casing (a), that comprises a handle (b) on which a trigger (c) is arranged, and a screen or display (h). Inside the casing (a) an image-capturing device (e) is arranged. A microcontroller (f) is arranged outside of the casing, but may alternatively be arranged inside the casing, and is connected to the trigger and the display, respectively, in order to proceed with the actuation of the device and the data display. Furthermore, inside the casing a lighting system and a light backscatter system (g) are provided to obtain a uniform image without optical aberration. The device of FIG. 1 further comprises a camera support (d).

Other components of the portable device (not shown in FIG. 1) are electric power- and data feeder cables, which transfer the captured image to a required portable personal computer. Furthermore, a polarizing lens can be added to reduce brightness, and a filter to correct the color temperature in the opening zone (i) of the image-capturing device (e). Surface (j) corresponds to the device portion that comes in contact with the sample to be analyzed.

Some relevant aspects to be considered for the measurement of meat quality parameters are meat origin (sheep, bovine or other meat), meat type, etc. in order to determine quality parameters properly.

Image analysis is performed on a computer by an image analyzing method, which has been particularly designed for this purpose and is actuated by capturing an image. The analysis of said image is performed and parameter results are displayed both on the screen of the computer and on the display of the device of the present invention, where said parameters were measured with user understandable units.

The indicated analysis performed by a certain method allows measurement of three quality parameters of meat such as meat texture, meat color, and intramuscular fat percentage. The values of each are displayed in a comprehensible form to the user (i.e. in measurement units used in foodstuffs science).

The method for obtaining said meat parameters begins with positioning and contacting the portable device to a meat specimen, where said portable device comprises a lighting system to homogenize the light inside said apparatus, and an image capturing device which captures a specimen image.

The method for obtaining meat quality parameters from an image is semi-automatic, as the method is controlled by a computational program that is run by the operator once the image capturing device is triggered. Said programming activates the image capturing device and subsequently processes the captured image and displays the processed image on a screen. Once the computational programming is run, it checks the device status, which includes verification of the status of the image capturing device, among others. Verification of the status of the image capturing device checks feeding status, memory status, communication with the computer, etc. If there is any erroneous parameter, the programming shows an error message; if not, said programming goes through an automatic configuration process of the device intended for the image capturing process. The configuration states image format, image storage location (which can be either a temporal location or a location for storing the corresponding image for future verifications), exposure time, focus adjust, diaphragm opening, white balance, etc. Once ready, the image is captured and stored in a previously selected address. Subsequently the programming checks the image capturing device once more.

In the present invention the artificial vision is used for determining meat quality parameters.

In order to perform the image analysis a technique using Artificial Neural Networks (ANN) is utilized. Artificial Neural Networks are capable of "learning", such as through back-propogation techniques, and due to this feature said artificial neural networks can transform data captured from an image into data of any other nature (conventional methods), such as data obtained by a Warner-Bratzler colorimeter, etc. Artificial Neural Networks (ANN) are prepared such that they can connect an inlet value to an outlet value. In the present invention said inlet value corresponds to a value obtained from data selected from the captured specimen image, whereas said outlet value refers to the result of the respective parameter, which is obtained by a physical or chemical method regarding the same specimen.

Outlet values for each parameter are intramuscular fat percentage, meat texture and color, which are determined by means of the following physical techniques:

Determination of Intramuscular Fat

The method of determining intramuscular fat percentage is based on the technique relating to the use of a graduated jig according to National Cattlemen's Beef Association; United States Department of Agriculture.

In said method a tag-blog is provided on the wet specimen which shows a squared grid drawn thereon. Then the operator proceeds to count those zones corresponding either to meat or fat inside said squared grid. Intramuscular fat percentage is calculated by means of a simple rule of three.

Texture Determination

The method for determining meat texture is based on Warner-Bratzler's technique.

From each meat cut cores cylinders, also referred as "cores", having a diameter of about 1.27 cm and a height of about 2.5 cm are obtained, wherein each cylinder shall be oriented parallel to muscle fibers. Then temperature is adjusted to 1-3° C., and subsequently said specimens are subjected to room temperature. After 5 minutes each cylinder (core) is sheared by means of a Warner-Bratzler probe executing a cut perpendicular to muscle fibers once at a rate of 200 mm/min and an approach rate of 80 mm/min and a pre-load of 0.01 Kg.F.

A texturometer having a maximum load cell of 500N (DO-FB05TS Model 2003, Zwick, Ulm, Germany) was utilized. Texture is expressed as Maximum Force at Kg.F with a mean value of 6 measurements.

Color Determination

Method for determining meat color was carried out by measuring specimen reflectance. Said reflectance analysis was performed on a Miniscan XE Plus model N° 45/0-1 Hunterlab, which utilizes CIELAB system expressing results in terms of variables L, a and b. Six measurements of each specimen are performed and made on the specimen surface. Equipment is programmed at an observation angle of 10° with illuminant D65, which is similar to daylight, using an absolute scale for coordinates L, a and b, wherein color is defined in a three-dimensional and spherical space. A mean value of the 6 measurements represent the value of each variable.

The image analyzing method comprises the following stages: color analysis, texture analysis, and analysis of meat fat percentage. The obtained results are finally displayed on screen in a user understandable manner.

Meat Texture Analysis

Texture analysis is performed by means of an analysis sub-routine, which begins with the recovery of an image stored in a defined address in the computer hard disc. To this, an image clustering function is applied, which cuts or segments the image to be analyzed, selecting from said image only areas representing a meat image, and the remaining elements are discarded (image background). Then the image is subdivided in several sub-images of less size, e.g., of 128× 128 pixels. Each of these images is analyzed to determine whether they correspond to meat or background (background is black; if image contains black pixels it will be discarded). Finally considered images are subjected to a Wavelet analysis by which a vector comprised of 8 RMS values for each sub-image or sub-area is obtained. Once this data is obtained and by means of a co-relation made by the prepared Artificial Neural Network, obtained variables are converted to a single shearing-force value. Obtained values for each image are averaged at a final stage, and said mean value, which is referred as $F_{TOTAL}$, is the value corresponding to the mean texture measurement.

Analysis of Intramuscular Fat Percentage

Another relevant parameter is the mean quality measurement, which corresponds to the intramuscular fat percentage contained in a meat cut.

The process for obtaining the value of intramuscular fat percentage begins with the recovery of an image stored in computer hard disc. Then the program accentuates interest zones of said image by means of simple linear and non-linear operations, such as multiplying the image by itself, filtering undesired brightness, adjusting intensity, etc. In this manner a superior contrast between image and background is reached. Image segmentation is then performed in order to separate background from the interest zone.

Image coordinates RGB are converted into coordinates CMY (better resolution) and then the colored image is converted into a gray-scale image. Subsequently a thresholding method is applied, which uses an adaptive method to look for the proper threshold according to a histogram of the image being analyzed in order to achieve a discrimination among different gray tones that correspond to white and black.

The white and black pixels are counted, thus obtaining fat and meat areas in the cut. Subsequently areas corresponding to fat and meat are calculated and they are converted into intramuscular fat percentage contained in the cut. This result is finally displayed on a screen.

Color Analysis of Meat Specimen

The color obtaining process begins with the recovery of an image stored in a computer hard disc. Subsequently the number of pixels of this image is reduced and then the image portion to be analyzed is segmented by means of a function referred to as clustering, considering meat zones only. From this image coordinates RGB are obtained, which are specimen representative. Then the artificial neural network converts RGB color space into XYZ color space of colored zones (meat zones) and differentiates colored zones through data co-relation to convert previous coordinates into XYZ coordinates, and then into CIE Lab coordinates. Finally CIE Lab coordinates are displayed and recorded, thus obtaining mean color of the analyzed meat cut and the program is ready to start again.

The invention claimed is:

1. A process for grading of meat such as bovine, porcine, sheep, poultry meat or others with no need to manipulate meat specimens, by means of a portable tool comprising an image-capturing device and an image analyzing method, wherein values of meat quality parameters including meat texture, intramuscular fat, and color are obtained due to management of data from a digitalized image of a meat specimen by an artificial neural network (ANN) system corresponding to a backpropagation type or one that can learn to convert data captured from the digitized image into data of other nature; and wherein the texture parameter of the meat specimen is obtained according to the following steps:

capturing an image;
  segmenting said image, where said segmentation stage only selects areas representing meat, and discards any remaining elements to produce a meat image;
  dividing said image into several sub-images having the same size;
  calculating a wavelet transform for each sub-image, from which a vector of RMS values is obtained for each sub-image; and
  co-relating in the ANN backpropagation, which relates each vector to a shear force value;
  calculating the mean value of the shear force values obtained for each sub-image.

2. The process for grading of meat according to claim 1, wherein the parameter of intramuscular fat of the meat specimen is obtained according to the following steps:

capturing an image;
  accentuating interest zones of said image by means of simple linear and non-linear operations, to obtain a superior contrast between image and background;

segmenting said accentuated image, where said segmentation stage only selects areas representing meat, to produce a meat image in red-green-blue (RGB) coordinates;
converting the RGB coordinates into cyan-magenta-yellow (CMY) coordinates;
converting the CMY coordinates into a gray-scale image;
classifying the gray-scale image into white and black pixels by means of adaptive thresholding;
counting the white and the black pixels; and
calculating percentages of fat, based on the white pixel count, and meat, based on the black pixel count.

3. The process for grading of meat according to claim 1, wherein the color parameter of the meat specimen is obtained according to the following steps:
capturing an image;
reducing the number of pixels of said image;
segmenting said image, where said segmentation stage only selects areas representing meat, to produce a meat image;
obtaining RGB coordinates from the meat image;
converting RGB coordinates into XYZ coordinates;
converting XYZ coordinates into CIE Lab coordinates;
associating color values in the CIE Lab coordinates with a colorimetry value using the neutral network system by means of a backpropagation ANN;
displaying on a screen the color parameter of the meat specimen.

4. A method for determining meat quality in an objective manner, comprising the use of a portable tool comprising a screen, which is approached to a meat specimen in order to capture an image, where said image is then analyzed by an objective method of image analysis to obtain a texture parameter of the meat specimen according to the following steps:
capturing an image;
segmenting said image, where said segmentation stage only selects areas representing a meat image, and discards the remaining elements;
dividing said image into several sub-images having the same size;
calculating a wavelet transform for each sub-image, from which a vector of RMS values is obtained for each sub-image; co-relating in an Artificial Neural Network (ANN) backpropagation, which relates each vector to a shear force value; calculating the mean value of values obtained from shear forces of each sub-image, and subsequently the meat texture parameter as determining the quality of the analyzed meat specimen is displayed on the screen of the tool.

* * * * *